United States Patent
Lindfors et al.

(10) Patent No.: US 7,394,537 B1
(45) Date of Patent: Jul. 1, 2008

(54) PRACTICAL LASER INDUCED BREAKDOWN SPECTROSCOPY UNIT

(75) Inventors: Pamela Lindfors, Espoo (FI); Mikko Krapu, Vantaa (FI)

(73) Assignee: Oxford Instruments Analytical Oy, Espoo (FI)

( * ) Notice: Subject to any disclaimer, the term of this patent is extended or adjusted under 35 U.S.C. 154(b) by 0 days.

(21) Appl. No.: 11/644,187

(22) Filed: Dec. 22, 2006

(51) Int. Cl.
*G01N 21/74* (2006.01)
*G01J 3/443* (2006.01)

(52) U.S. Cl. .................................................. 356/318
(58) Field of Classification Search ................. 356/318, 356/316
See application file for complete search history.

(56) References Cited

U.S. PATENT DOCUMENTS

| | | | | |
|---|---|---|---|---|
| 4,550,381 | A * | 10/1985 | Waechter et al. | 250/369 |
| 4,986,658 | A * | 1/1991 | Kim | 356/318 |
| 5,379,103 | A * | 1/1995 | Zigler | 356/73 |
| 5,583,634 | A | 12/1996 | Andre et al. | |
| 5,608,520 | A * | 3/1997 | Fleming | 356/318 |
| 5,781,289 | A * | 7/1998 | Sabsabi et al. | 356/318 |
| 5,798,832 | A * | 8/1998 | Hnilica et al. | 356/316 |
| 5,946,089 | A * | 8/1999 | Duer | 356/318 |
| 6,407,811 | B1 | 6/2002 | Snyder et al. | 356/316 |
| 6,424,416 | B1 * | 7/2002 | Gross et al. | 356/326 |
| 6,700,660 | B2 * | 3/2004 | Sabsabi et al. | 356/318 |
| 6,741,345 | B2 * | 5/2004 | Sabsabi et al. | 356/318 |
| 6,762,835 | B2 * | 7/2004 | Zhang et al. | 356/318 |
| 6,762,836 | B2 * | 7/2004 | Benicewicz et al. | 356/318 |
| 6,801,595 | B2 | 10/2004 | Grodzins et al. | |
| 6,836,325 | B2 * | 12/2004 | Maczura et al. | 356/328 |
| 6,909,505 | B2 * | 6/2005 | Lucas et al. | 356/318 |
| 6,986,739 | B2 * | 1/2006 | Warren et al. | 600/159 |
| 7,016,035 | B2 * | 3/2006 | Wu et al. | 356/318 |
| 7,092,087 | B2 * | 8/2006 | Kumar et al. | 356/318 |
| 7,236,243 | B2 * | 6/2007 | Beecroft et al. | 356/328 |
| 2004/0200341 | A1 * | 10/2004 | Walters et al. | 89/1.13 |
| 2006/0078019 | A1 | 4/2006 | Wang et al. | |
| 2006/0262302 | A1 | 11/2006 | Eklin | |

(Continued)

OTHER PUBLICATIONS

DeLucia, F.C., Jr.; Samuels, A.C.; Harmon, R.S.; Walters, R.A.; McNesby, K.L.; LaPointe, A.; Winkle, R.J.,Jr.; and Miziolek, A.W.; Laser-Induced Breakdown Spectroscopy (LIBS): A Promising Versatile Chemical Sensor Technology for Hazardous Material Detection, Aug. 2006, IEEE Sensors Journal, vol. 5, No. 4, pp. 681-689.*

(Continued)

*Primary Examiner*—Gregory J Toatley, Jr.
*Assistant Examiner*—Bryan Giglio
(74) *Attorney, Agent, or Firm*—Wood, Phillips, Katz, Clark & Mortimer

(57) ABSTRACT

An apparatus for performing laser-induced breakdown spectroscopy comprises a handheld unit with a pump laser and a controller. A combination of a solid laser medium and a Q-switch receive a laser beam from said pump laser. Focusing optics focus laser pulses from said combination to a focal spot at a sample. Light collection optics collect light from plasma induced of sample material by focused laser pulses. A spectrometer receives collected light and produces information describing its spectral distribution. A power source delivers electric power to other parts of the apparatus. The pump laser, combination, focusing optics, light collection optics, spectrometer and power source are parts of said handheld unit.

17 Claims, 2 Drawing Sheets

U.S. PATENT DOCUMENTS

2006/0262900 A1 11/2006 Sipila et al.
2007/0296967 A1* 12/2007 Gupta et al. .............. 356/318

OTHER PUBLICATIONS

Harmon, R.S.; DeLucia, F.C., Jr.; LaPointe, A.; and Miziolek, A.W.; Man-Portable LIBS for Landmine Detection, Jun. 2006, Proc. Of SPIE, vol. 6217, p. 621701-1-621701-7.*

Bohling, C.; Scheel, D.; Hohmann, K.; Schade, W.; Reuter, M.; and Holl, G.; Fiber-optic laser sensor for mine detection and verification, Jun. 2006, Applied Optics, vol. 45, No. 16.*

Walters, Roy A. (Powerpoint, Unknown Material Analysis in Less Than A Second: Man Portable LIBS, Ocean Optics, Oct. 6, 2006, http://www. researchcaucus.org/presentations/default.asp) comprises a visual presentation of the HP-LIBS device. The webpage showing the date presented is included.*

Pierce, et al. (Pierce, W. and Christian, S.M., Portable LIBS Instrumentation can identify trace levels of environmental pollutants, Photonik International, 2006, Originally published in German in Photonik Jan. 2005) comprises a suitcase sized portable LIBS device.*

Applied Photonics, Ltd., Portable LIBS Instrument Model No. 0117—Users Manual, Nov. 2006, p. 1-10.*

Pierce, W.; Christian, S.M.; Myers, M.J.; Myers, J.D.:, Field-testing for environmental pollutants using briefcase sized portable LIBS system; LIBS_2004, 3rd International Conference on Laser Induced Plasma Spectroscopy and Applications, 2004, p. 1-14.*

B.L. Volodin, S.V. Dolgy, E.D. Melnik, E. Downs, J. Shaw and V.S. Ban: "Wavelength Stabilization and Spectrum Narrowing of High-Power Multimode Laser Diodes and Arrays by Use of Volume Bragg Gratings".

* cited by examiner

PRACTICAL LASER INDUCED BREAKDOWN SPECTROSCOPY UNIT

TECHNICAL FIELD

The invention concerns in general the technology of laser-induced breakdown spectroscopy. In particular the invention concerns the structure of an apparatus built for laser-induced breakdown spectroscopy measurements.

BACKGROUND OF THE INVENTION

For various applications, methods are needed for determining the material constitution of a sample. One of known methods is laser-induced breakdown spectroscopy (LIBS), which involves focusing a laser beam onto a surface of the sample with a high enough power density to transform a small part of the sample material into a state of plasma. Optical emissions from the plasma plume are collected with light collection optics, and the spectral distribution (i.e. intensity as a function of wavelength) of the collected optical emissions is analysed in a spectrometer that produces information in electronic form describing the spectral distribution. Since atomic and molecular constituents of sample materials have characteristic optical emission spectra, the information produced by the spectrometer forms a kind of a fingerprint of the sample material, revealing the constituents of that part of the sample onto which the laser beam was focused.

The sample may in principle be solid, liquid or gaseous. In the case of a gaseous sample the concept of a "surface" of the sample does not exist, but the laser beam is just focused into the gaseous sample.

LIBS is sometimes also referred to as OES (optical emission spectroscopy), although to be quite exact, the latter is a somewhat wider term and may be understood to cover all kinds of optical emission measurements, irrespective of the mechanism that was used to generate the optical emissions.

Prior art publications that describe LIBS measurements are at least U.S. Pat. No. 5,583,634 and U.S. Pat. No. 6,801,595, of which the latter describes the combination of a LIBS measurement with an XRF (X-ray fluorescence) measurement in the same measurement apparatus. A drawback of the known LIBS measurement devices is certain clumsiness and limited applicability to field use. Traditionally LIBS has been considered to be applicable under laboratory conditions only.

An objective of the present invention is to present a LIBS measurement arrangement and devices that are practical to handle and applicable to field use. Another objective of the invention is to enable LIBS measurements of sample forms and locations that would be difficult or impossible to reach with conventional LIBS measurement devices.

The objectives of the invention are achieved by including all essential components of a LIBS measuring arrangement into a single hand-held unit. Certain further objectives of the invention are easiest to reach by using a passive probe that contains the so-called Q-switch, focusing optics and light collection optics.

An apparatus according to the invention for performing laser-induced breakdown spectroscopy is characterised in that it comprises:
  a handheld unit,
  a pump laser with a controller,
  a combination of a solid laser medium and a Q-switch configured to receive a laser beam from said pump laser,
  focusing optics configured to focus laser pulses from said combination to a sample,
  light collection optics configured to collect light from plasma induced of sample material by focused laser pulses,
  a spectrometer configured to receive collected light from said light collection optics and to produce information describing a spectral distribution of such light, and
  a power source configured to deliver electric power to other parts of the apparatus;

wherein said pump laser, said combination, said focusing optics, said light collection optics, said spectrometer and said power source are parts of said handheld unit.

The exceptionally high power density that is needed to create plasma is reached by Q-switching, most typically passive Q-switching. It involves using a piece of optical gain medium in connection with a saturable absorber, also known as the passive Q-switch. A saturation effect in the absorber leads to a rapid reduction of resonator loss, so that energy temporarily stored in the gain medium is instantaneously extracted in the form of a laser pulse. The cycle of storing and releasing energy is repeated at a rate determined by the pumping power and the characteristics of the saturable absorber.

Passively Q-switched pulse lasers have been considered to only be suitable to benchtop analysers, because their energy consumption has been relatively high. However, in the course of the development work leading to the present invention it was found that certain means may be applied to significantly reduce the energy consumption. Using Nd:YLF (Neodymium (3+)-doped Yttrium Lithium Fluoride) as the active (gain) medium leads to better efficiency, higher pulse energy and shorter pulse duration, which means that in order to create the same amount of plasma, the electric power needed for the pump laser can be smaller than with e.g. a corresponding Nd:YAG (Neodymium (3+)-doped Yttrium Aluminum Garnet) gain medium. Wavelength locking can be used to stabilize the output wavelength of the laser diode, which substantially eliminates temperature-dependent wavelength drift. This way the power-intensive active temperature control of the pump laser can be completely avoided or at least limited to only compensating for the largest deviations from a nominal operating temperature.

The (passive) Q-switch, focusing optics and light collection optics may be placed in a separate probe part, with an optical fiber cable connecting it to a main part of the measurement device. Such a separate probe part may be very sleek in appearance, so that samples and locations that would be impossible or inconvenient to reach with the whole handheld measurement apparatus can still be reached with the probe.

The exemplary embodiments of the invention presented in this document are not to be interpreted to pose limitations to the applicability of the appended claims. The verb "to comprise" is used in this document as an open limitation that does not exclude the existence of also unrecited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF EMBODIMENTS OF THE INVENTION

Figure 1:
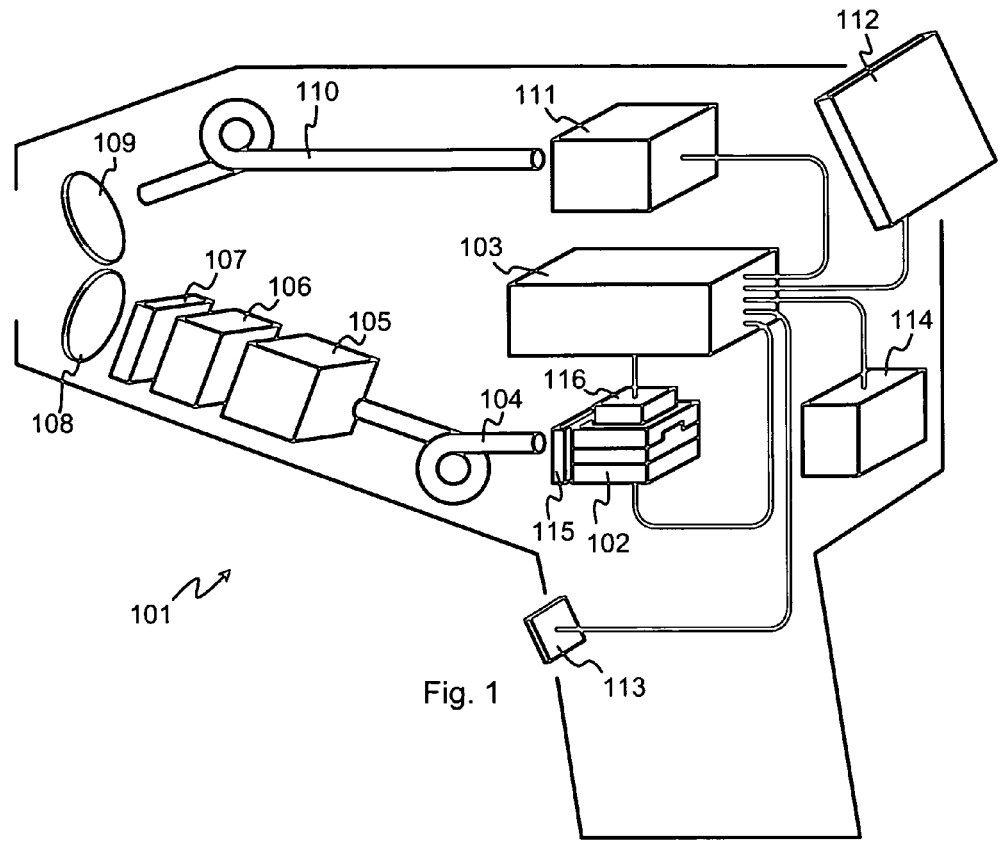
FIG. 1 illustrates schematically a measurement apparatus according to an embodiment of the invention.

FIG. 1 illustrates schematically a handheld unit 101, which has a size and shape that enable a human user to easily carry it along in the purpose of making LIBS measurements. Inside the handheld unit 101 is a pump laser 102, which here is schematically shown as a laser diode. A controller 103 is arranged to control the operation of the pump laser 102. An optical fiber 104 conducts the laser light emitted by the pump laser 102 to a combination of a solid laser medium 105 and a Q-switch 106, which is typically a passive Q-switch but may also be an active one. Together the solid laser medium 105 and the Q-switch constitute a Q-switched pulse laser, the output pulses of which are directed through an outcoupling mirror 107 and focusing optics 108 towards a sample (not shown).

A person skilled in the art understands that the linear arrangement of the Q-switched pulse laser, which is schematically illustrated in FIG. 1, is not the only possible alternative. A linear arrangement means here that the output laser pulses are emitted along a line that geometrically is a direct extension of the line along which the pump laser radiation is directed to the solid laser medium 105. Other geometrical arrangements include, but are not limited to, one in which the pump laser radiation comes through an obliquely placed one-way mirror and the other end of the cavity of the Q-switched pulse laser is 100% reflective, so that the output pulses are reflected to an angle by said obliquely placed one-way mirror.

Optical emissions from a sample (not shown) are collected through collecting optics 109 and conveyed through an optical fiber 110 to a spectrometer 111, which produces information in electronic form describing the spectral distribution of the optical emissions. This information is forwarded to the controller 103, which processes and stores the information and may provide visual indications illustrative of said information on a display 112. In addition to the display 112, the user interface of the apparatus may comprise various switches, of which a trigger switch 113 is schematically shown. The operating power needed to operate the apparatus comes from a power source 114, which may be e.g. a rechargeable battery or a fuel cell.

The apparatus of FIG. 1 should be designed to have good efficiency, one criterion of which is the ratio of output pulse power to the power used to operate the pump laser. It is possible to use Nd:YAG (Neodymium (3+)-doped Yttrium Aluminum Garnet) as the solid laser medium 105, but better efficiency results if Nd:YLF (Neodymium (3+)-doped Yttrium Lithium Fluoride) is used instead. The invention does not exclude the use of other kinds of solid laser media, especially if other materials are found that provide an even higher efficiency. Taken that the Q-switch 106 is a passive Q-switch, it may be made e.g. of Cr:YAG (Chromium (4+)-doped Yttrium Aluminum Garnet) or other material suitable for use as a saturable absorber. If an active Q-switch is used, any applicable technology such as acousto-optic or electro-optic modulation is possible.

In the absence of any compensating action the output wavelength of the laser diode that is used as the pump laser in FIG. 1 would exhibit a relatively strong dependency on temperature (typically in the order of 0.3 nm/K). Laser diodes are not lossless, which means that during operation their temperature tends to increase. Traditionally a LIBS apparatus has included active temperature control functions to stabilize the temperature of the pump laser. However, using a peltier element or the like to actively keep a laser diode at a constant temperature consumes relatively high amounts of power, especially because the efficiency of known peltier elements is modest.

The spectral line width of typical laser diodes is in the order of 2-4 nm, which is somewhat too wide because the width of the absorption peak in the solid laser medium is narrower, in the order of 0.8-2 nm, and all emissions of the pump laser that do not come on the absorption wavelengths represent a waste of energy.

According to an aspect of the present invention, using a wavelength locking system, which helps to keep the output wavelength constant irrespective of changes in temperature, may enhance the overall efficiency of the system. In many cases the wavelength locking system may double as means for narrowing the output spectral line width of the laser diode, which provides a further increase in efficiency. The wavelength locking and spectral line narrowing system is schematically represented in FIG. 1 as the element 115, which is a wavelength-selective device positioned in the optical path of the laser beam that feeds a narrow portion of the laser emission back into the cavity of the pump laser 102. Devices of this kind are known for example from the publication B. L. Volodin, S. V. Dolgy, E. D. Melnik, E. Downs, J. Shaw, and V. S. Ban: "Wavelength stabilization and spectrum narrowing of high-power multimode laser diodes and arrays by use of volume Bragg gratings", Optics Letters, Vol. 29, No. 16, pp. 1891-1893, Optical Society of America, Aug. 15, 2004. Other known wavelength-locking systems are the so-called Fabry-Perot filters.

The invention does not exclude the use of an active temperature control arrangement, and indeed one is schematically shown as element 116 in FIG. 1. However, due to the use of a wavelength locking and spectral line narrowing system, the active temperature control arrangement does not need to keep the temperature of the pump laser 102 within as tight limits as in conventional LIBS devices. One possibility is to only switch on the active temperature control arrangement if the temperature of the pump laser would otherwise exceed a maximum operating temperature, like +50° C. An indication of said wavelength locking and spectral line narrowing system not being able to keep said output wavelength constant without additional thermal control could come e.g. from a temperature sensor (not shown) that keeps the controller 103 aware of the current operating conditions.

Figure 2:
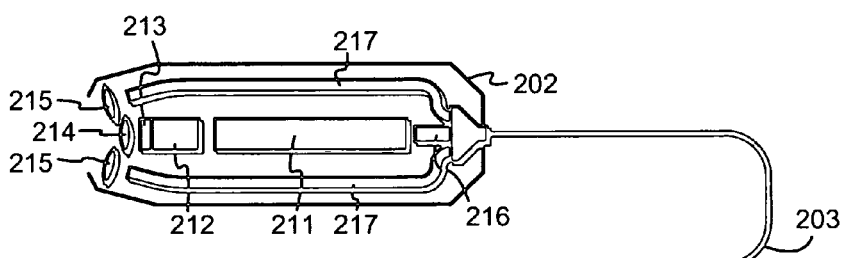
FIG. 2 illustrates schematically a measurement apparatus according to another embodiment of the invention.
Figure 2:
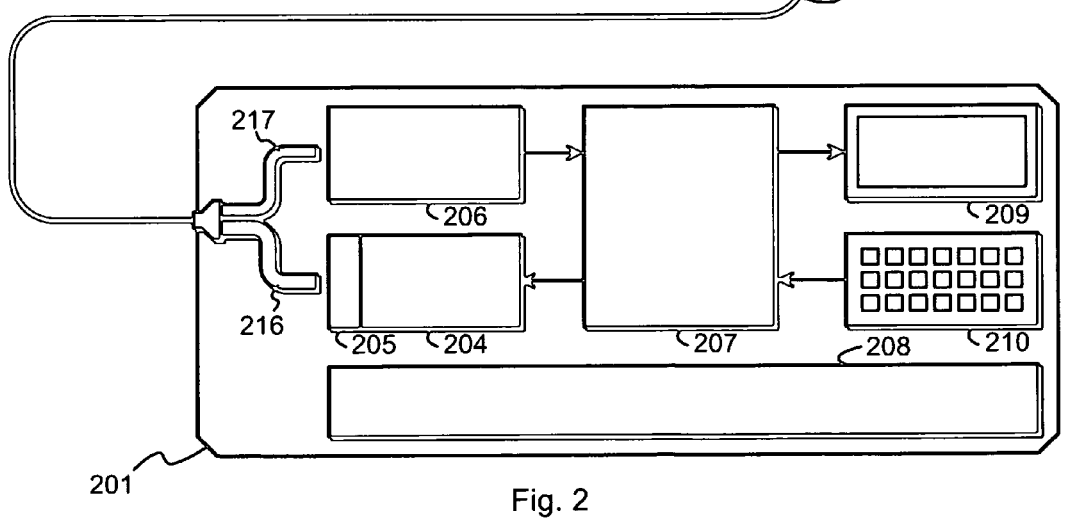

FIG. 2 illustrates schematically a measurement apparatus according to another embodiment of the invention. The handheld unit comprises a body part 201 and a probe part 202. A cable 203 couples the probe part 202 to the body part 201. The body part 201 comprises a pump laser 204 equipped with a wavelength locking system 205, which may also have the function of narrowing the output spectral line width of the pump laser 204. Additionally the body part 201 comprises a spectrometer 206, a controller 207, a power source 208, and a user interface which here is schematically shown to comprise a display 209 and keys 210. Although FIG. 2 does not show any temperature controlling arrangement in the body part 201 for controlling the temperature of the pump laser 204, one may naturally exist.

The probe part 202 comprises a Q-switched pulse laser that comprises a combination of a solid laser medium 211 and a Q-switch 212 and that is equipped with an outcoupling mirror 213. Additionally the probe part 202 comprises focusing optics 214 and light collection optics 215. The probe part 202 may be a completely passive device, if a passively Q-switched pulse laser is used. Thus the cable 203 does not need to include any wires that would conduct electricity. On the other hand, the invention does not exclude using in the probe part active components or other devices that need electric current, like indicator LEDs or electrically controllable shutters. In such cases it is most straightforward to use wires that form a part of the cable 203 to conduct electricity between the probe part and the body part.

As a part of the cable 203, a first optical fiber cable 216 is configured to convey laser light from the pump laser 204 in the body part 201 to the combination of solid laser medium 211 and Q-switch 212 in the probe part 202. A return optical fiber cable 217 in the cable 203 is configured to convey collected light from the light collection optics 215 in the probe part 202 to the spectrometer 206 in the body part 201. Here the light collection optics 215 have been distributed around the focusing optics 214, for which reason the return optical fiber cable 217 has several branches in that end that is inside the probe part 202.

The body part 201 may comprise e.g. a shoulder strap or other means for making it easy to carry the body part along. The probe part 202 has a size and shape that make it easy to hold the probe part 202 in one hand and to place the business end thereof against a sample to be measured. According to another embodiment, the body part 201 comprises a holder (not shown) for removably attaching the probe part 202 to the body part 201, so that the user may decide, whether he keeps the probe part attached to the body part 201 and uses the combination as the entity that is brought close enough to the sample to make the measurement, or whether he detaches the probe part and only brings the probe part close enough to the sample to make the measurement.

Creating a protective gas atmosphere around the measurement area can in many cases enhance the performance of LIBS measurements. This is especially true if the sample constituents include carbon and/or other materials that react very actively with oxygen and/or nitrogen when they are in the state of plasma. Since an objective in using a protective gas atmosphere is to restrain reactions, inert (noble) gases are very suitable for this purpose.

In order not to sacrifice the portability of the apparatus, it is advantageous to build a gas administration subsystem that it contains a relatively small gas container included in or attachable to the handheld unit, a conduit for allowing gas from said gas container to flow to the measurement area, and a controllable valve for regulating the amount of gas to be administered. Said controllable valve may function under the same controller that receives the user's operating commands through the user interface, and also controls the operation of the pump laser.

Figure 3:
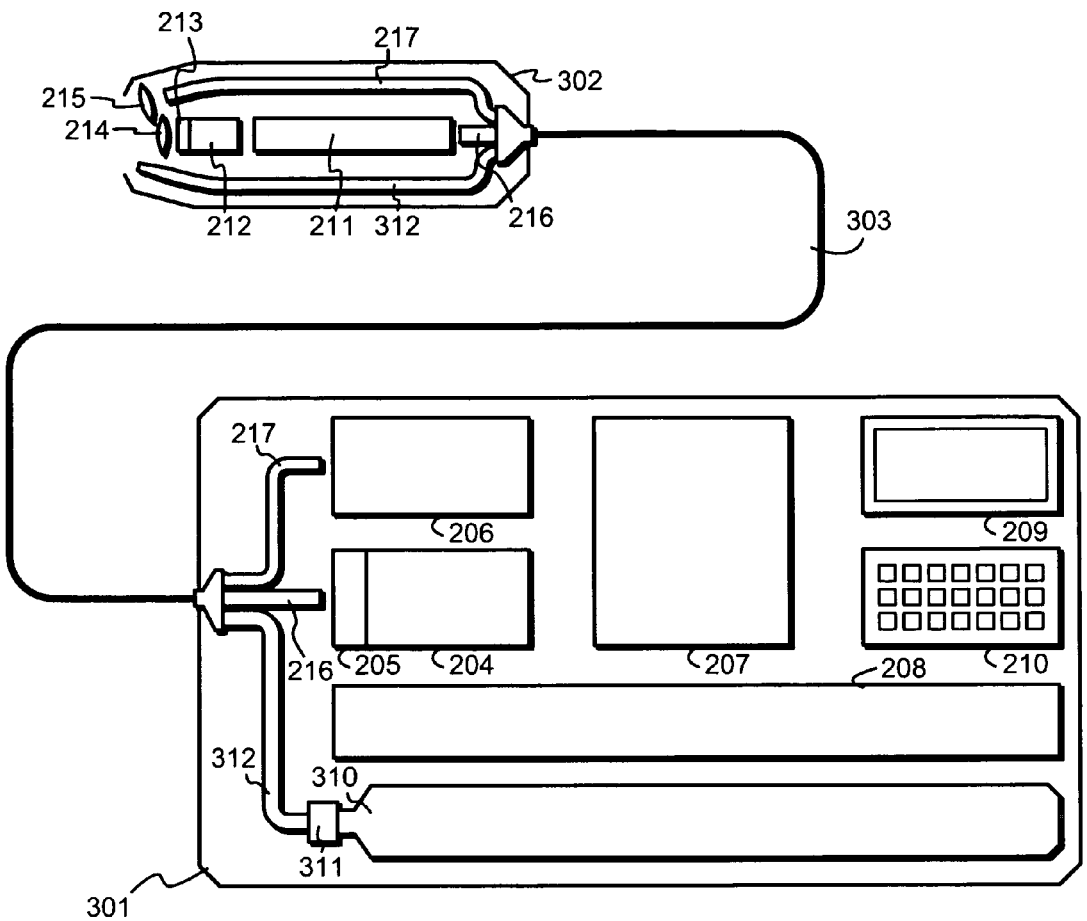
FIG. 3 illustrates schematically a measurement apparatus according to yet another embodiment of the invention.

FIG. 3 illustrates schematically a measurement device according to an embodiment of the invention, in which a gas administration subsystem exists. Parts with the same reference designators are similar to the corresponding parts in FIG. 2, with the small exception that the return optical fiber cable 217 is only shown to have one branch within the probe part 302. The body part 301 comprises a gas container 310, which may be e.g. a refillable container or a removable, disposable gas cartridge. A controllable valve 311 regulates the flow of gas from the gas container 310 through a conduit 312, which constitutes a part of the cable 303, to the business end of the probe part 302. When a user gives through the keys 210 or other input means a command for beginning a measurement, the controller 207 begins a sequence in which it first allows gas from the gas container 310 to flow to the measurement area for a pre-programmed duration of time and then begins the actual measurement. If the cable between the body part and the probe part contains wires or other means for passing control signals and operating power, a controllable valve may also exist in the probe part.

It is clear to a person skilled in the art that a gas administration subsystem can be built also in a handheld measurement apparatus that does not have a separate probe part but has all functionalities built within a single entity.

Figure 4:
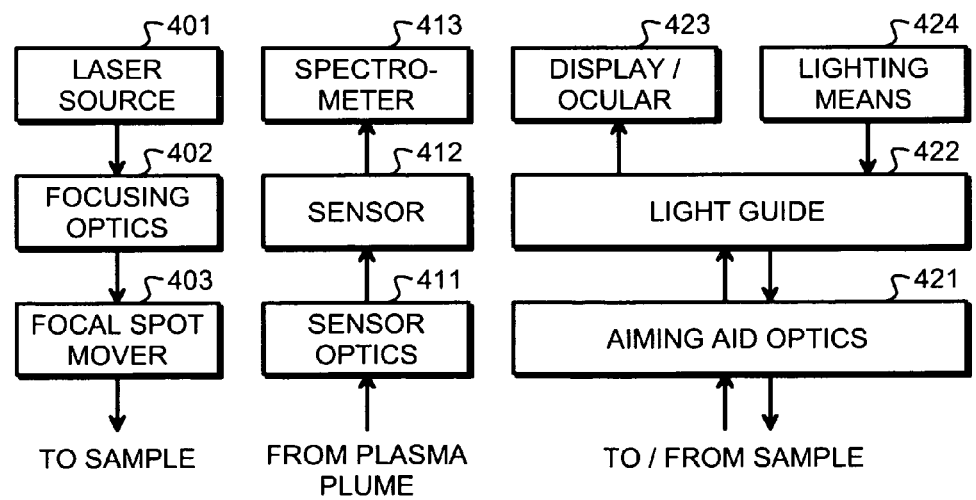
FIG. 4 illustrates schematically some optical aspects of a measurement apparatus according to an embodiment of the invention.

FIG. 4 illustrates certain optical aspects of a measurement apparatus according to an embodiment of the invention. The laser source 401 is a Q-switched pulse laser. Instead of a single laser source it is possible to use two or more laser sources producing laser light on different wavelengths, or a single laser source and one or more nonlinear optical crystals such as Potassium Titanyl Phosphate (KTP) crystals and appropriate timing, to vary the way in which the optical stimulus is provided to the sample. With frequency multipliers it is possible to change the initial infrared range wavelength of the plasma-inducing laser light to e.g. one half or one quarter of the original wavelength.

Focusing optics 402 may include, in a way very well known as such, optical elements such as lenses, mirrors, slits, grids, collimators and the like. The task of the focusing optics 402 is to focus the output beam of the laser source 401 onto the surface of a sample. Relatively gentle changes in beam diameter, synonymous with relatively long focal length, are preferred because measurement apparatuses of the kind meant in the invention are frequently used in field conditions, where it is not possible to require very exact positioning of the sample in relation to the measurement head. A long focal length helps to reduce the effect of variations in measurement geometry. However, even if in this context the focal length can be said to be long if it allows an uncertainty of submillimeter scale in sample positioning, it should be understood that in a macroscopic scale (at distances larger than a few millimeters) and from the point of view of a user operating the measurement apparatus, the plasma-inducing laser diverges so quickly and has such a harmless wavelength that radiation hazards to the environment are negligible. Due to the expected difficulties in positioning the sample very exactly we may define that the focal spot is "on the surface of the sample" if it is close enough to the surface (in- or outside the sample material) to allow the formation of plasma.

According to an aspect of the invention there is provided a focal spot mover 403, the task of which is to move the focal spot of the plasma-inducing laser beam across the surface of a sample for a distance that is large compared with the diameter of the focal spot. The purpose of moving the focal spot is to cover a more representative portion of the sample material than what happens to be within the area of the focal spot. Additionally moving the focal spot prevents repeated laser pulses from eating away the surface of the sample material at one point. Although the size of the "drilling hole" created by a stationary focal spot would be so small that it would seldom be even visible, let alone cause any actual disadvantage, the drilling effect may involve other drawbacks for example in applications where the measurement is aimed at investigating the very surface of a sample the material composition of which varies as a function of depth.

Due to the very short duration of each single laser pulse, the movement of the focal spot during a single pulse is negligible and can be omitted. However, when pulses are repeated for a measurement duration in the order of a few seconds, even a relatively simple focal spot mover arrangement is capable of making the focal spot traverse a significant distance, in the order of one millimeter or a few millimeters. The physical implementation of the focal spot mover 403 may involve e.g. an electrically moved mirror or a rotating lens. The movement of the focal spot on the sample surface may be oscillatory, so that it travels e.g. a linear track back and forth or along a circular or elliptical track. The electric power needed to operate the focal spot mover comes from the power subsystem of the measurement apparatus and the moving is accomplished under the control of the controller. It may be advisable to allow the user to have some online control over the way in which the focal spot is moved, especially if the sample to be investigated is so small or heterogeneous that moving the focal spot might involve the risk of making it wander out of the actual area of interest. Such control is most advantageously combined with the aiming aid discussed in more detail below.

Sensor optics 411 are provided for collecting optical emissions from a plasma plume induced at the focal spot and for directing the collected optical emissions to the optical sensor 412. In their simplest form the sensor optics 411 consist of a free passage of light between the sample surface and the sensor 412. More elaborate solutions may include for example lenses, mirrors, light guides and other optical elements. In order to keep reflected quanta of the incident laser radiation from interfering with the detection of optical emissions it is advantageous to use an infrared filter as a part of the sensor optics 411. A normal Nd:YAG microlaser produces incident radiation at the wavelength of about 1060 nm, which is in the infrared range, so it is effectively filtered out by an infrared filter.

The sensor 412 detects the optical emissions collected by the sensor optics 411. In order to provide meaningful results the sensor 412 must be sensitive to wavelength and intensity. However, these requirements are relatively easily filled. A line of photodiodes, similar to those used in regular barcode scanners, is often sufficient. In this graphical representation, the sensor 412 is separate from the spectrometer 413; in FIGS. 1, 2, and 3 the combination has been illustrated schematically with a single block called the spectrometer. Together, the sensor 412 and the spectrometer 413 constitute an arrangement adapted to convert the collected optical emissions into an electronic signal representative of the spectral distribution and intensity of the optical emissions. If a focal point mover is used to move the focal spot of the plasma-inducing laser, the detection process must be adapted to take into account the corresponding changes in measurement geometry. This can be easily accomplished for example by using the movable mirror that causes the focal spot to move also as a part of the sensor optics 411.

According to an aspect of the invention, the measurement apparatus comprises an optical aiming aid adapted to provide the user with visual feedback about the location on the sample surface that will be subjected to measurement. An image of the appropriate part of the sample surface is conducted through aiming aid optics 421 and a light guide 422 to a display or ocular 423, which we will designate as the display device. In order to ensure sufficient lighting of the sample it is advisable to provide lighting means 424, from which light can be taken through the light guide 422 and aiming aid optics 421 to the target area on the sample surface. According to a first alternative, the lighting means 424 produce a general background lighting in order to provide a sufficiently bright image of the target area on the sample surface to the display device. Other aiming means, such as frames and/or crosshairs, can then be used to indicate, exactly which point on the sample surface the laser beam from the laser source 401 will hit.

According to another alternative, the lighting means 424 may comprise another laser source, which in contrast to the plasma-inducing laser source 401 is adapted to produce a laser beam in the visible wavelength range. This visible laser beam can be focused through the light guide 422 and the aiming aid optics 421 onto the sample surface, where its reflection constitutes a visible indicator spot that shows, which point on the sample surface the laser beam from the laser source 401 will hit. In order to keep the indicator laser from interfering with the optical measurement it is advisable to make its operation controllable so that it will be shut off during the optical measurement. Alternatively filtering arrangements can be utilized.

The light guide 422, the aiming aid optics 421, the focusing optics 402 and the focal spot mover 403 may include shared components. For example, also the visible laser beam originating from the lighting means 424 may be directed through the focal spot mover 403 in order to move the indicator spot on the sample surface in a manner that is similar to the movement of the focal spot of the plasma-inducing laser beam. This way the user can easily check, in the case of a very small or very heterogeneous sample, that the movement of the focal spot will not take it outside the area of interest. If the movement caused by the focal spot mover 403 is controllable, the user may first check it by using the indicator spot and by changing e.g. the extent or direction of linear movement or the radius of a circular movement so that only an appropriate target area of the sample surface will be covered by the movement of the focal spot. Controlling the movement caused by the focal spot mover 403 necessitates movement-controlling input means in the user interface of the measurement apparatus, as well as a coupling from these to a part of the control subsystem that actually controls the focal spot mover 403.

The embodiments of the invention that have been described above are exemplary and do not limit the interpretation of the appended claims.

We claim:

1. An apparatus for performing laser-induced breakdown spectroscopy, comprising:
    a handheld unit,
    a pump laser with a controller,
    a wavelength locking system configured to keep an output wavelength of said pump laser essentially constant irrespective of temperature of said pump laser,
    a combination of a solid laser medium and a Q-switch configured to receive a laser beam from said pump laser,
    focusing optics configured to focus laser pulses from said combination to a focal spot at a sample,
    light collection optics configured to collect light from plasma induced of sample material by focused laser pulses,
    a spectrometer configured to receive collected light from said light collection optics and to produce information describing a spectral distribution of such light, and
    a power source configured to deliver electric power to other parts of the apparatus;
wherein said pump laser, said combination, said focusing optics, said light collection optics, said spectrometer and said power source are parts of said handheld unit.

2. An apparatus according to claim 1, wherein said Q-switch is a passive Q-switch, and said combination comprises said solid laser medium, a saturable absorber and a coupling mirror.

3. An apparatus according to claim 2, wherein said active medium comprises Neodymium (3+)-doped Yttrium Aluminum Garnet, and the saturable absorber comprises Chromium (4+)-doped Yttrium Aluminum Garnet.

4. An apparatus according to claim 2, wherein said active medium comprises Neodymium (3+)-doped Yttrium Lithium Fluoride.

5. An apparatus according to claim 1, comprising an active temperature control arrangement configured to regulate a temperature of said pump laser.

6. An apparatus according to claim 5, wherein said active temperature control arrangement is configured to actively regulate a temperature of said pump laser as a response to an indication of said wavelength locking system not being able to keep said output wavelength constant without additional thermal control.

7. An apparatus according to claim 1, comprising a probe part coupled to a body part of said handheld unit through a cable.

8. An apparatus according to claim 7, wherein:
said pump laser is located in said body part of said handheld unit, and
said combination, said focusing optics and said light collection optics are located in said probe part.

9. An apparatus according to claim 8, wherein said cable comprises a first optical fiber cable configured to convey laser light from said pump laser in said body part to said combination in said probe part.

10. An apparatus according to claim 9, wherein said cable comprises a return optical fiber cable configured to convey collected light from said light collection optics in said probe part to said spectrometer in said body part.

11. An apparatus according to claim 1, comprising a gas administration subsystem configured to controllably deliver gas to a space around a focal spot at which said focusing optics are configured to focus said laser pulses.

12. A measurement apparatus according to claim 1, comprising an optical aiming aid adapted to provide a user with visual feedback about the location of said focal spot on said surface of said sample.

13. A measurement apparatus according to claim 12, wherein said optical aiming aid comprises:
a display device and
aiming aid optics and a light guide adapted to conduct an image of a part of the sample surface to said display device.

14. A measurement apparatus according to claim 13, comprising aiming means adapted to indicate on said display device at which point on the sample surface the focal spot will be.

15. A measurement apparatus according to claim 13, comprising a source of laser light of visible wavelength adapted to illuminate a spot on said surface of said sample, said illuminated spot being coincident with said focal spot.

16. An apparatus for performing laser-induced breakdown spectroscopy, comprising:
a handheld unit,
a pump laser with a controller,
an active temperature control arrangement configured to regulate a temperature of said pump laser,
a combination of a solid laser medium and a Q-switch configured to receive a laser beam from said pump laser,
focusing optics configured to focus laser pulses from said combination to a focal spot at a sample,
light collection optics configured to collect light from plasma induced of sample material by focused laser pulses,
a spectrometer configured to receive collected light from said light collection optics and to produce information describing a spectral distribution of such light, and
a power source configured to deliver electric power to other parts of the apparatus;
wherein said pump laser, said combination, said focusing optics, said light collection optics, said spectrometer and said power source are parts of said handheld unit.

17. An apparatus for performing laser-induced breakdown spectroscopy, comprising:
a handheld unit comprising a body part and a probe part coupled to said body part through a cable,
a pump laser with a controller,
a combination of a solid laser medium and a Q-switch configured to receive a laser beam from said pump laser,
focusing optics configured to focus laser pulses from said combination to a focal spot at a sample,
light collection optics configured to collect light from plasma induced of sample material by focused laser pulses,
a spectrometer configured to receive collected light from said light collection optics and to produce information describing a spectral distribution of such light, and
a power source configured to deliver electric power to other parts of the apparatus;
wherein said pump laser is located in said body part of said handheld unit; and wherein said combination, said focusing optics and said light collection optics are located in said probe part; and wherein said spectrometer and said power source are parts of said handheld unit.

* * * * *